United States Patent
Meyer et al.

(10) Patent No.: US 6,916,932 B2
(45) Date of Patent: Jul. 12, 2005

(54) REDUCTIVE CLEAVAGE OF THE EXOCYCLIC ESTER OF UK-2A OR ITS DERIVATIVES AND PRODUCTS FORMED THEREFROM

(75) Inventors: Kevin Gerald Meyer, Zionsville, IN (US); Carl Vincent DeAmicis, Indianapolis, IN (US); Normohamed Mohamed Niyaz, Indianapolis, IN (US); Richard Brewer Rogers, Mobile, AL (US); Gina Marie Fitzpatrick, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 10/483,947

(22) PCT Filed: Jul. 31, 2002

(86) PCT No.: PCT/US02/24204

§ 371 (c)(1),
(2), (4) Date: Jan. 15, 2004

(87) PCT Pub. No.: WO03/011857

PCT Pub. Date: Feb. 13, 2003

(65) Prior Publication Data

US 2004/0171838 A1 Sep. 2, 2004

Related U.S. Application Data

(60) Provisional application No. 60/308,939, filed on Jul. 31, 2001.

(51) Int. Cl.$^7$ ............................................. C07D 405/00
(52) U.S. Cl. ................................................... 546/281.7
(58) Field of Search ...................................... 546/281.7

(56) References Cited

U.S. PATENT DOCUMENTS

2004/0048864 A1 * 3/2004 Ricks et al. ................. 514/247

FOREIGN PATENT DOCUMENTS

WO          01/14339           3/2001

OTHER PUBLICATIONS

Greene, et al. Protective Groups in Organic Synthesis, John Wiley & Sons, Inc. 1991, pp. 98–99.
M. Ueki, et al., UK–2A, B, C, D, Novel Antifungal Antibiotics from *Streptomyces* sp. 517–02 Journal of Antibiotics 1996, 49, 639.

* cited by examiner

*Primary Examiner*—Cecilia J. Tsang
*Assistant Examiner*—Binta Robinson
(74) *Attorney, Agent, or Firm*—Lynn Zettler

(57) ABSTRACT

A process comprising reacting compound GF-I with a reducing agent to form compound GF-II wherein Y is selected from the group consisting of H, benzyl, substituted benzyl, $CH_2OC_{1-8}$ alkyl, $CH_2OC_{3-8}$ cycloalkyl, allyl, tetrahydropyranyl, tetra-hydrofuranyl, substituted tetrahydropyranyl, substituted tetra-hydrofuranyl, $Si(C_{1-4}$ alkyl$)_3$, and $Si(Ph)_x(C_{1-4}$ alkyl$)_{3-x}$ where x is equal to 1, 2 or 3; and wherein said process is conducted: (a) in the presence of a reducing agent; (b) in the presence of an aprotic solvent; and (c) under reaction conditions; is provided. Additionaly, novel compounds produced therefrom are provided text:

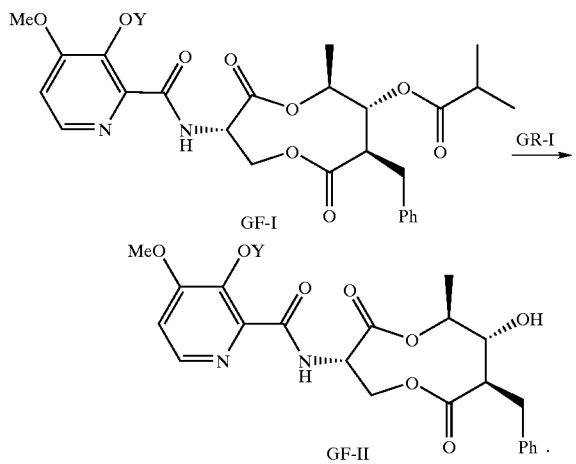

17 Claims, No Drawings

REDUCTIVE CLEAVAGE OF THE EXOCYCLIC ESTER OF UK-2A OR ITS DERIVATIVES AND PRODUCTS FORMED THEREFROM

This application claims the benefit of Provisional Application No. 60/308,939, filed Jul. 31, 2001.

FIELD OF THE INVENTION

This invention is related to the field of processes used to cleave an ester from a compound, and is also related to the field of compounds that may be used as fungicides, and is also related to the field of compounds that can be used to produce compounds that can be used as fungicides.

BACKGROUND OF THE INVENTION

UK-2A is a natural product having the following formula.

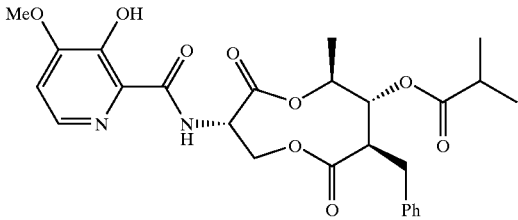

UK-2A is described in M. Ueki, et al. *J Antibiot.* 1996, 49, 639. While this compound has certain properties that make it useful in a variety of fields, currently, it is being investigated as a starting point for making compounds that have efficacy in the fungicide area.

SUMMARY OF THE INVENTION

It is an object of this invention to provide a process to reductively cleave the exocyclic ester of UK-2A or its derivatives and to produce novel compounds, which are useful intermediates in the synthesis of biologically active materials.

In accordance with this invention a process is provided. Said process comprises reacting compound GF-I with a reducing agent to form compound GF-II. Additionally, novel compounds produced therefrom are claimed.

For the purposes of this application the following terms have the following meanings. The term "Ph" means phenyl. The term "Me" means methyl. The term "EtOAc" means ethyl acetate. The term "ppm" refers to parts per million. The term "psia" refers to pounds per square inch absolute. The term "m.p." refers to melting point. Throughout this document, all temperatures are given in degrees Celsius (° C.), all percentages are weight percentages, all melting points are uncorrected, unless otherwise stated.

DETAILED DESCRIPTION OF THE INVENTION

In reaction GR-I

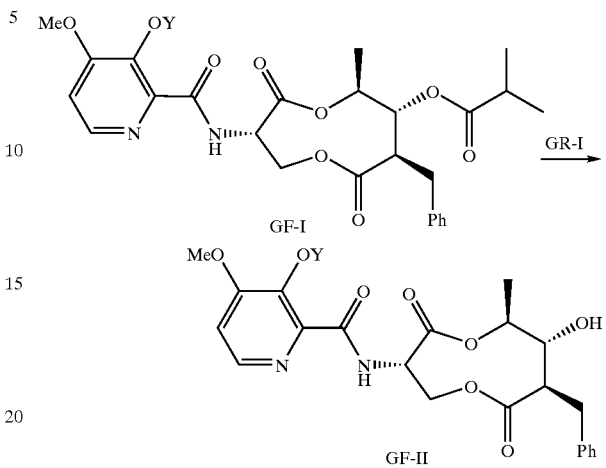

Y is selected from the group consisting of H, benzyl, substituted benzyl, $CH_2OC_{1-8}$ alkyl, $CH_2OC_{3-8}$ cycloalkyl, allyl, tetrahydropyranyl, tetrahydrofuranyl, substituted tetrahydropyranyl, substituted tetrahydrofuranyl, $Si(C_{1-4}$ alkyl$)_3$, and $Si(Ph)_x(C_{1-4}$ alkyl$)_{3-x}$ where x is equal to 1, 2, or 3.

The term "substituted benzyl" means a benzyl group having one or more substituents. The substituents on the ring of the substituted benzyl are called "Ring Substituents". Ring Substituents are selected from the group consisting of halo (F, Cl, and Br), $C_{1-8}$ alkoxy, $C_{2-8}$ alkenoxy, $C_{5-8}$ cycloalkoxy, and phenyloxy. The substituents on the methylene carbon of the substituted benzyl are called "Methylene Substituents". Methylene Substituents are $C_{1-3}$ alkyl. Each of the Ring and Methylene Substituents that have one or more hydrogens, may have one or more of such hydrogens replaced with a halogen (F, Cl, and Br).

The terms "substituted tetrahydropyranyl" and "substituted tetrahydrofuranyl" mean a tetrahydropyranyl or tetrahydrofuranyl substituted with one or more substituents selected from the group consisting of halo (F, Cl, and Br), $C_{1-8}$ alkyl, $C_{1-8}$ alkoxy, $C_{2-8}$ alkenoxy, $C_{5-8}$ cycloalkoxy, and phenyloxy. Each of these substituents that have one or more hydrogens, may have one or more of such hydrogens replaced with a halogen (F, Cl, and Br).

Examples of silyl compounds include, but are not limited to, $Si(t-Bu)Me_2$, $Si(Ph)Me_2$, $SiEt_3$, and $SiMe_3$.

Currently, Y is preferably H or benzyl, with H being most preferred.

A reducing agent is used in reaction GR-I. Currently, any hydride with the correct reduction potential to remove the ester may be used. Suitable examples of such hydrides are: (1) $R^1R^2HAl$; (2) $R^1R^2R^3AlHM$; and (3) $R^1R^2R^3BHM$. In these hydrides $R^1$, $R^2$, $R^3$ are independently selected from the group consisting of H, $C_{1-8}$ alkyl, hetero $C_{1-8}$ alkyl, $C_{1-8}$ alkoxy, and hetero $C_{1-8}$ alkoxy. The term "hetero" in hetero $C_{1-8}$ alkyl and hetero $C_{1-8}$ alkoxy means a molecular structure containing 1–8 carbon atoms and 1–3 oxygen or sulfur atoms in the main chain of the molecular structure. Examples of these molecular structures include, but are not limited to, $CH_3CH_2OCH_2CH_2—$, $CH_3OCH_2CH_2OCH_2CH_2—$, and $CH_3CH_2SCH_2—$, M is selected from the group consisting of Na, Li, K, Ca, Zn. Currently, it is preferred to use diisobutylaluminum hydride.

Currently, it is preferred to have an excess of reducing agent to GF-I. It is more preferred to have about 3 to about 4 moles of reducing agent to GF-I depending upon Y. If Y is H it is preferred to have about 4 moles of reducing agent per mole of GF-I. If Y is not H it is preferred to have about 3 moles of reducing agent per mole of GF-I.

The reaction is conducted in an aprotic solvent. The solvent can be selected from the group consisting of tetrahydrofuran, 1,4-dioxane, dichloromethane, toluene, di($C_{1-8}$ alkyl) ether, $C_{5-8}$ alkanes, $C_{3-8}$ cycloalkanes, 1,2-dichloroethane, benzene, substituted benzene, glyme, diglyme, or mixtures thereof. The term "substituted benzene" means a benzene substituted with one or more substituents selected from the group consisting of halo (F, Cl, and Br), $C_{1-3}$ alkyl, $C_{1-8}$ alkoxy, $C_{2-8}$ alkenoxy, $C_{5-8}$ cycloalkoxy, and phenyloxy.

The reaction conditions comprise a temperature from about −80° C. to about 50° C., preferably about −25° C. to about 25° C. Currently, pressure is not considered to be critical and a pressure from about ambient to about 50 psia may be used. In general, it is best to run the reaction with the components substantially in the liquid state.

After the reaction is substantially complete, the product GF-II is recovered from the reaction mixture. This can be accomplished by first quenching the reaction by adding water, alcohol, ester, ketone, or an aldehyde (examples include, but are not limited to, methanol, ethyl acetate, and acetone). This is followed by using a mineral acid (examples include, but are not limited to, HCl and $H_2SO_4$) to promote separation of the reaction mixture components. This is then followed by extracting compound GF-II into an organic solvent. Examples of such organic solvent include, but are not limited to, EtOAc and methylene chloride.

EXAMPLES

These examples are provided to illustrate the invention. They are not meant to be construed as limiting the invention.

Natural product UK-2A (1) or the benzyl ether (2) were subjected to diisobutylaluminum hydride in methylene chloride ($CH_2Cl_2$) at reduced or ambient temperature to provide the des-isobutyryl derivatives 3 and 4.

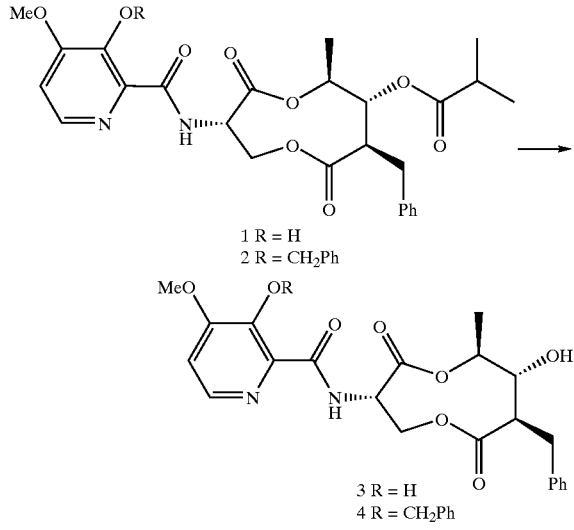

Preparation of (3S, 6S, 7R, 8R)-8-benzyl-3-({[3-(benzyloxy)-4-methoxypyridin-2-yl]carbonyl}amino)-6-methyl-4,9-dioxo-1,5-dioxonan-7-yl 2-methylpropanoate (2)

Benzyl bromide (0.233 mol, 27.7 mL) was added to a solution of NaI (0.097 mol, 14.5 g) in acetone (1 L). Natural product UK-2A (1) (0.194 mol, 100 g) was added followed by powdered $K_2CO_3$ (0.388 mol, 53 g) and the mixture stirred vigorously overnight. The mixture was diluted with $CH_2Cl_2$ (500 mL) and washed with $H_2O$ (2×500 mL). The organic layer was dried ($MgSO_4$), and concentrated in vacuo. Recrystallization (EtOAc/hexane) gave 95.5 g (79%) of 2 as an off-white solid (m.p. 169–170° C.) which contained ~6.5% N-benzylated product (LC-MS). $^1$H-NMR and MS (M+1 605) were consistent for the title compound (2). The compound was used in the next step without further purification. The N-benzylated by-product could be removed from the mixture prior to recrystallization by filtration of the crude reside through a plug of silica gel (30% acetone/hexane as the eluent).

Preparation of N-[(3S, 7R, 8R, 9S)-7-benzyl-8-hydroxy-9-methyl-2,6-dioxo-1,5-dioxonan-3-yl]-3-(benzyloxy)-4-methoxypyridine-2-carboxamide (4)

Diisobutylaluminum hydride (1.0 M in $CH_2Cl_2$, 24.8 mmol) was added dropwise to a −78° C. solution of (2) (8.27 mmol, 5.0 g) in $CH_2Cl_2$ (40 mL). The mixture was stirred an additional 15 min, quenched with EtOAc (200 mL) and warmed to ambient temperature. Hydrochloric acid (2N, 100 mL) was added slowly and stirred vigorously for 15 min. The layers were separated and the organic layer dried ($MgSO_4$) and concentrated in vacuo. The residue was purified by chromatography (1% acetic acid/acetone) to give 1.54 g (35%) of 4 as a glassy, white solid, m.p. 110–114° C. $^1$H-NMR and MS (M+1 535) were consistent with the desired product.

Preparation of N-[(3S,7R,8R,9S)-7-benzyl-8-hydroxy-9-methyl-2,6-dioxo-1,5-dioxonan-3-yl]-3-hydroxy-4-methoxypyridine-2-carboxamide (3)

Diisobutylaluminum hydride (1.0 M in $CH_2Cl_2$, 23.3 mmol) was added dropwise to a 20° C. solution of natural product UK-2A (1) (5.8 imol, 3.0 g) in $CH_2Cl_2$ (60 mL). The mixture was stirred an additional 15 min and quenched with EtOAc (10 mL). Hydrochloric acid (2N, 100 mL) was added slowly and stirred vigorously for 15 min. The layers were separated and the organic layer dried ($MgSO_4$) and concentrated in vacuo to give 1.82 g (70%) of 3 as a foamy, light yellow solid. $^1$H NMR (300 MHz, $CDCl_3$): δ 11.82 (s, 1H), 8.63 (d, J=8.2 Hz, 1H), 8.01 (d, J=5.2 Hz, 1H), 7.32–7.20 (m, 5H), 6.89 (d, J=5.2 Hz), 5.35 (m, 1H), 5.16 (m, 1H), 4.86 (m, 1H), 3.96 (s, 3H), 3.76 (t, J=9.4 Hz, 1H), 3.62 (m, 1H), 3.25 (m, 1H), 3.02 (m, 1H), 2.77 (m, 1), 1.51 (d, J=6.3 Hz, 3H); $^{13}$C NMR (MHz, $CDCl_3$): δ 173.2, 170.2, 169.4, 155.8, 149.2, 141.1, 138.8, 130.3, 129.2, 129.0, 127.0, 110.1, 77.6, 77.2, 65.4, 56.5, 54.4, 50.3, 35.4, 18.7 ppm; IR (KBr pellet): 3370 (br), 2966, 1751, 1654, 1529, 1453, 1263, 1045, 801 $cm^{-1}$; Exact Mass: n/z calcd. for $C_{22}H_{24}N_2O_8$ $[M]^+$= 444.1533, found 444.1513.

We claim:

1. A process comprising reacting compound GF-I with a reducing agent to form compound GF-II

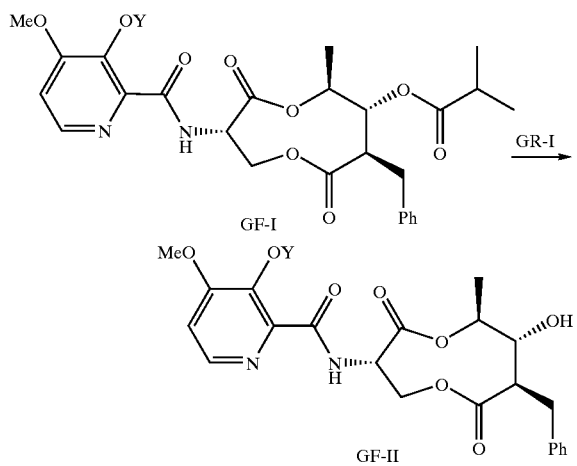

wherein Y is selected from the group consisting off H, benzyl, substituted benzyl, $CH_2OC_{1-8}$ alkyl, $CH_2OC_{3-8}$ cycloalkyl, allyl, tetrahydropyranyl, tetrahydrofuranyl, substituted tetrahydropyranyl, substituted tetrahydrofuranyl, $Si(C_{1-4}$ alkyl$)_3$, and $Si(Ph)_x$ $(C_{1-4}$ alkyl$)_3$ where x is equal to 1, 2, or 3; and wherein said process is conducted:

(a) in the presence of a reducing agent;
(b) in the presence of an aprotic solvent: and
(c) at a temperature from about −80° C. to about 50° C.

2. A process according to claim 1 wherein Y is selected from the group consisting of H and benzyl.

3. A process according to claim 1 wherein said reducing agent has a general formula selected from the group consisting of $R^1R^2HAl$, $R^1R^2R^3AlHM$ or $R^1R^2R^3BHM$, and wherein $R^1$, $R^2$, $R^3$ are independently selected from the group consisting of H, $C_{1-8}$ alkyl, hetero $C_{1-8}$ alkyl, $C_{1-8}$ alkoxy, and hetero $C_{1-8}$ alkoxy, and wherein the term "hetero" in hetero $C_{1-8}$ alkyl and hetero $C_{1-8}$ alkoxy means a molecular structure containing 1–8 arbon atoms and 1–3 oxygen or sulfur atoms in the main chain of the molecular structure, and wherein M is selected from the group consisting of Na, Li, K, Ca, and Zn.

4. A process according to claim 1 wherein said reducing agent is diisobutylaluminum hydride.

5. A process according to claim 1 wherein an excess of reducing agent to GE-I is used.

6. A process according to claim 1 wherein about 3 to about 4 moles of reducing agent to GF-I is used.

7. A process according to claim 1 wherein Y is H and about 4 moles of reducing agent per mole of GE-I is used.

8. A process according to claim 1 wherein Y is not H and about 3 moles of reducing agent per mole of GF-I is used.

9. A process according to claim 1 wherein said aprotic solvent is selected from the group consisting of tetrahydrofuran, 1,4-dioxane, dichioromethane, toluene, di($C_{1-8}$ alkyl) ether, $C_{5-8}$ alkanes, $C_{3-8}$ cycloalkanes, 1,2-dichloroethane, benzene, substituted benzene, glyme, diglyme, or mixtures thereof.

10. A process according to claim 1 wherein said aprotic solvent is selected from the group consisting of dichioro methane toluene or mixtures thereof.

11. A process according to claim 1 wherein said reaction conditions comprise a temperature from about −25° C. to about 25° C.

12. A process according to claim 1:
(1) wherein Y is selected from the group consisting of H and benzyl;
(2) wherein said reducing agent has a general formula selected from the group consisting of $R^1R^2Hal$, $R^1R^2R^3AlHM$ or $R^1R^2R^3BHM$, wherein $R^1$, $R^2$, $R^3$ are independently selected from the group consisting of H, $C_{1-8}$ alkyl, hetero $C_{1-8}$ alkyl, $C_{1-8}$ alkoxy, and hetero $C_{1-8}$ alkoxy, and wherein the term "hetero" in hetero $C_{1-8}$ alkyl and hetero $C_{1-8}$ alkoxy means a molecular structure containing 1–8 carbon atoms and 1–3 oxygen or sulfur atoms in the main chain of the molecular structure, and wherein M is selected from the group consisting of Na, Li, K, Ca, and Zn;
(3) wherein an excess of reducing agent to GF-I is used;
(4) wherein said aprotic solvent is selected fro the group consisting of tetrahydrofuran, 1,4-dioxane, dichloromethane, toluene, di($C_{1-8}$ alkyl) ether, $C_{5-8}$ alkanes, $C_{3-8}$ cycloalkanes, 1,2-dichloroethane, benzene, substituted benzene, glyme, diglyme, or mixtures thereof.

13. A process according to claim 1:
(1) wherein Y is selected from the group consisting of H and benzyl;
(2) wherein said reducing agent is diisobutylaluminum hydride;
(3) wherein about 3 to about 4 moles of reducing agent to GF-I is used;
(4) wherein said aprotic solvent is selected from the group consisting of dichloromethane, toluene, or mixtures thereof.

14. A compound GF-II

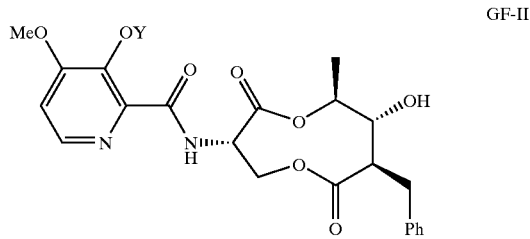

wherein Y is selected from the group consisting of H, benzyl, substituted benzyl, $CH_2OC_{1-8}$ alkyl, $CH_2OC_{3-8}$ cycloalkyl, allyl, tetrahydropyranyl, tetrahydrofuranyl, substituted tetrahydropyranyl, substituted tetrahydrofuranyl, $Si(C_{1-4}$ alkyl$)_3$, and $Si(Ph)_x(C_{1-4}$ alkyl$)_{3-x}$ where x is equal to 1, 2, or 3.

15. A compound according to claim 14 wherein Y is selected from the group consisting of H and benzyl.

16. A compound according to claim 14 wherein Y is H.

17. A compound according to claim 15 wherein Y is benzyl.

* * * * *

UNITED STATES PATENT AND TRADEMARK OFFICE
CERTIFICATE OF CORRECTION

PATENT NO. : 6,916,932 B2
DATED : July 12, 2005
INVENTOR(S) : Kevin Gerald Meyer et al.

It is certified that error appears in the above-identified patent and that said Letters Patent is hereby corrected as shown below:

Column 5,
Line 21, should read -- ...wherein Y is selected from the group consisting of H... -- rather than "...wherein Y is selected from the group consisting off H...".
Line 52, should read -- ...about 4 moles of reducing agent per mole of GF-I is used." rather than "...about 4 moles of reducing agent per mole of GE-I is used.".

Column 6,
Line 21, should read -- (4) wherein said aprotic solvent is selected from the group... -- rather than "(4) wherein said aprotic solvent is selected fro the group...".

Signed and Sealed this

Fourth Day of October, 2005

JON W. DUDAS
*Director of the United States Patent and Trademark Office*